(12) United States Patent
Terai et al.

(10) Patent No.: US 12,217,867 B2
(45) Date of Patent: Feb. 4, 2025

(54) MEDICAL INFORMATION PROCESSING SYSTEM AND MEDICAL INFORMATION PROCESSING APPARATUS

(71) Applicant: CANON MEDICAL SYSTEMS CORPORATION, Otawara (JP)

(72) Inventors: Koichi Terai, Shioya-gun (JP); Yasunari Kutsuna, Nasushiobara (JP); Shouichi Nogawa, Shioya-gun (JP); Hisaya Shirakane, Shinagawa (JP); Jyunichi Yoshida, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 776 days.

(21) Appl. No.: 17/212,289

(22) Filed: Mar. 25, 2021

(65) Prior Publication Data

US 2021/0304894 A1 Sep. 30, 2021

(30) Foreign Application Priority Data

Mar. 26, 2020 (JP) .................................. 2020-056658

(51) Int. Cl.
*G16H 10/60* (2018.01)
*G16H 30/20* (2018.01)
*G16H 30/40* (2018.01)
*G16H 50/20* (2018.01)

(52) U.S. Cl.
CPC ............ *G16H 50/20* (2018.01); *G16H 10/60* (2018.01); *G16H 30/20* (2018.01); *G16H 30/40* (2018.01)

(58) Field of Classification Search
CPC .................................................. A61B 5/7267
See application file for complete search history.

(56) References Cited

U.S. PATENT DOCUMENTS

| 10,002,311 B1* | 6/2018 | Garnavi ................. G06N 3/044 |
| 2007/0237377 A1* | 10/2007 | Oosawa ................ G16H 50/20 382/128 |
| 2011/0301982 A1* | 12/2011 | Green, Jr. .............. G16H 40/67 705/3 |
| 2013/0152020 A1* | 6/2013 | Nishiyama ............ G16H 30/20 715/835 |

(Continued)

FOREIGN PATENT DOCUMENTS

WO  WO 2019/150813 A1  8/2019

*Primary Examiner* — Di Xiao
(74) *Attorney, Agent, or Firm* — Oblon, McClelland, Maier & Neustadt, L.L.P.

(57) ABSTRACT

A medical information processing system according to an embodiment of the present disclosure includes a first processing circuit configured: to cause a display circuit to display a first image obtained by a medical image diagnosis apparatus; to cause the display circuit to display a plurality of regions classified in correspondence with a plurality of diseases and to display, in each of the plurality of regions, a representative image related to a corresponding one of the diseases; to receive a correspondence operation to bring the first image displayed by the display circuit into correspondence with one of the plurality of regions; and to cause, in response to the correspondence operation, a storage circuit to store therein, with respect to each of the diseases, the first image displayed by the display circuit as a verification requiring image related to the disease corresponding to the region brought into correspondence therewith.

19 Claims, 7 Drawing Sheets

(56) References Cited

U.S. PATENT DOCUMENTS

| | | | |
|---|---|---|---|
| 2017/0256082 A1* | 9/2017 | Nabatame | G06F 3/0486 |
| 2018/0137244 A1* | 5/2018 | Sorenson | A61B 8/565 |
| 2019/0171914 A1* | 6/2019 | Zlotnick | G06F 18/41 |
| 2020/0160981 A1* | 5/2020 | Masubuchi | G06N 3/08 |
| 2020/0342267 A1 | 10/2020 | Usuda | |

* cited by examiner

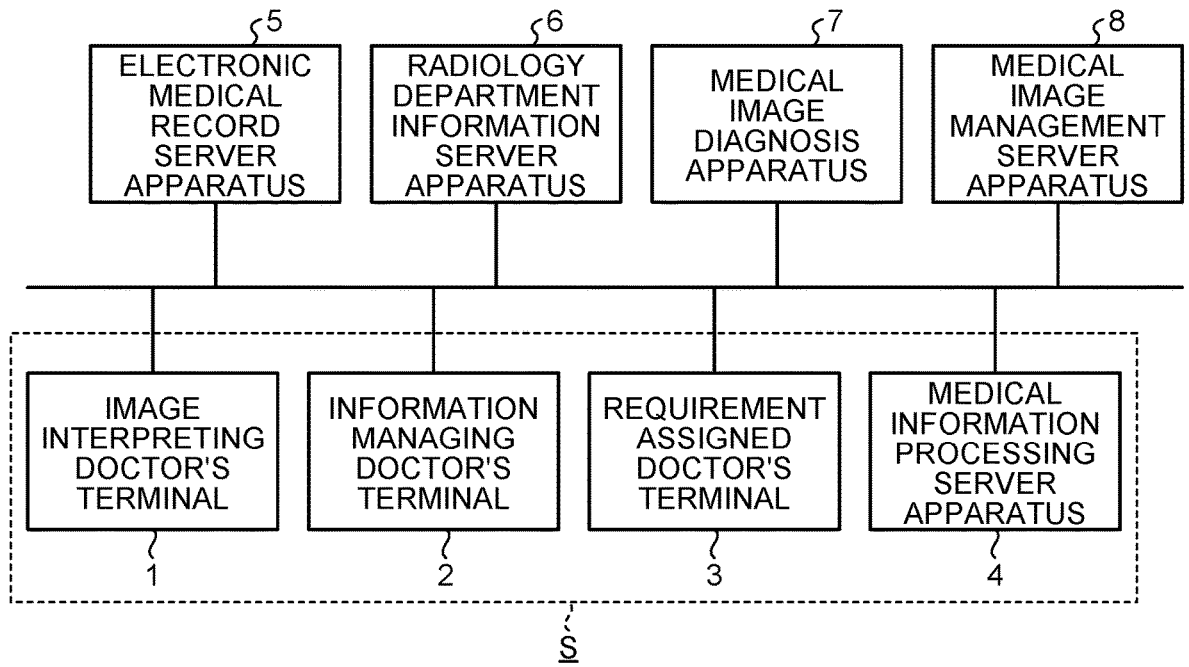
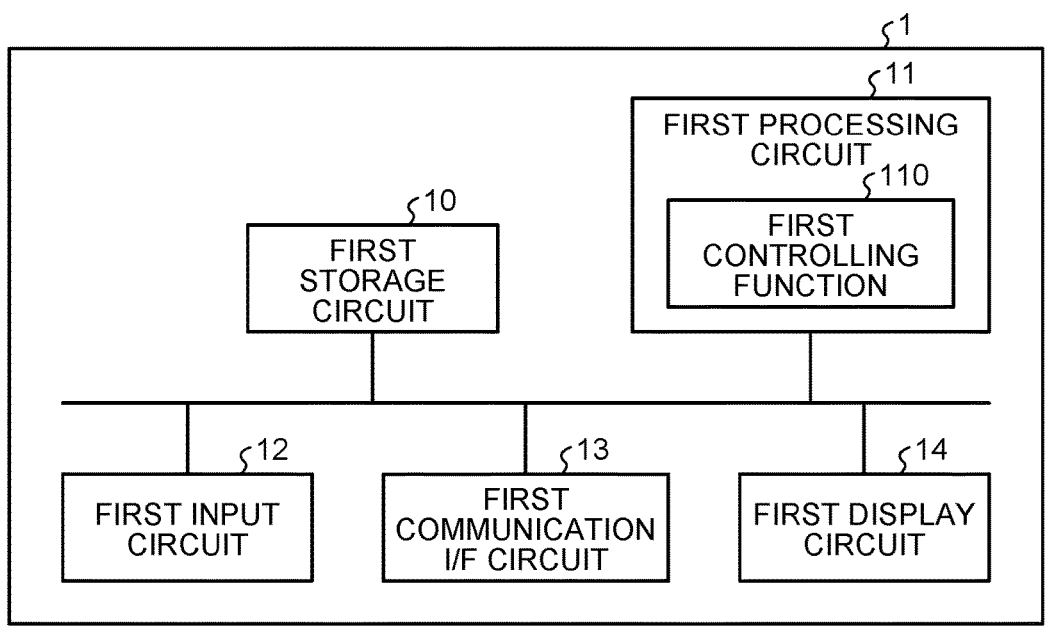

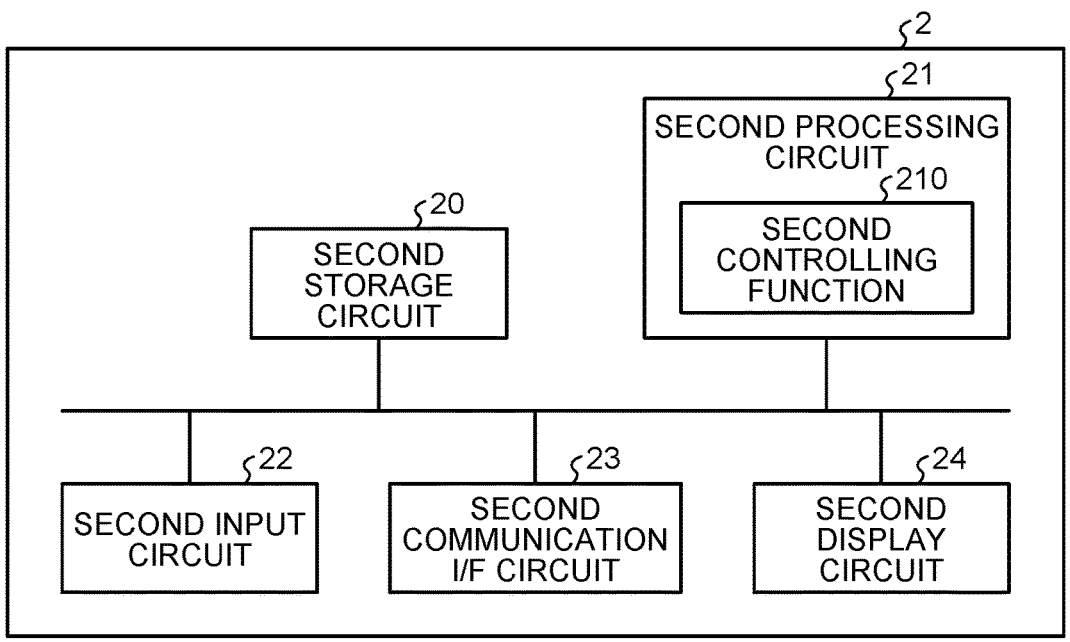

| RELEVANT OBSERVATION | DATA | CONTOUR EXTRACTION | RESULT OF PATHOLOGICAL EXAMINATION | APPROVAL ON IMAGE DIAGNOSIS RESULT | FINAL REGISTRATION |
|---|---|---|---|---|---|
| STROKE | IMAGE A | OK | OK | OK | OK |
| LUNG NODULE | IMAGE B | OK | N/A | OK | REGISTER ~72 |
| BREAST CANCER | IMAGE C | OK | OK | : | : |
| ⋮ | ⋮ | | ⋮ | | |

| REQUIREMENT PROCESSING | PATIENT ID | EXAMINA-TION DATE | ... | REQUEST-ING DOCTOR |
|---|---|---|---|---|
| STROKE CONTOUR EXTRACTION | IMAGE A | | | |
| | IMAGE B | | | |
| | IMAGE C | | | |
| | ⋮ | | | |

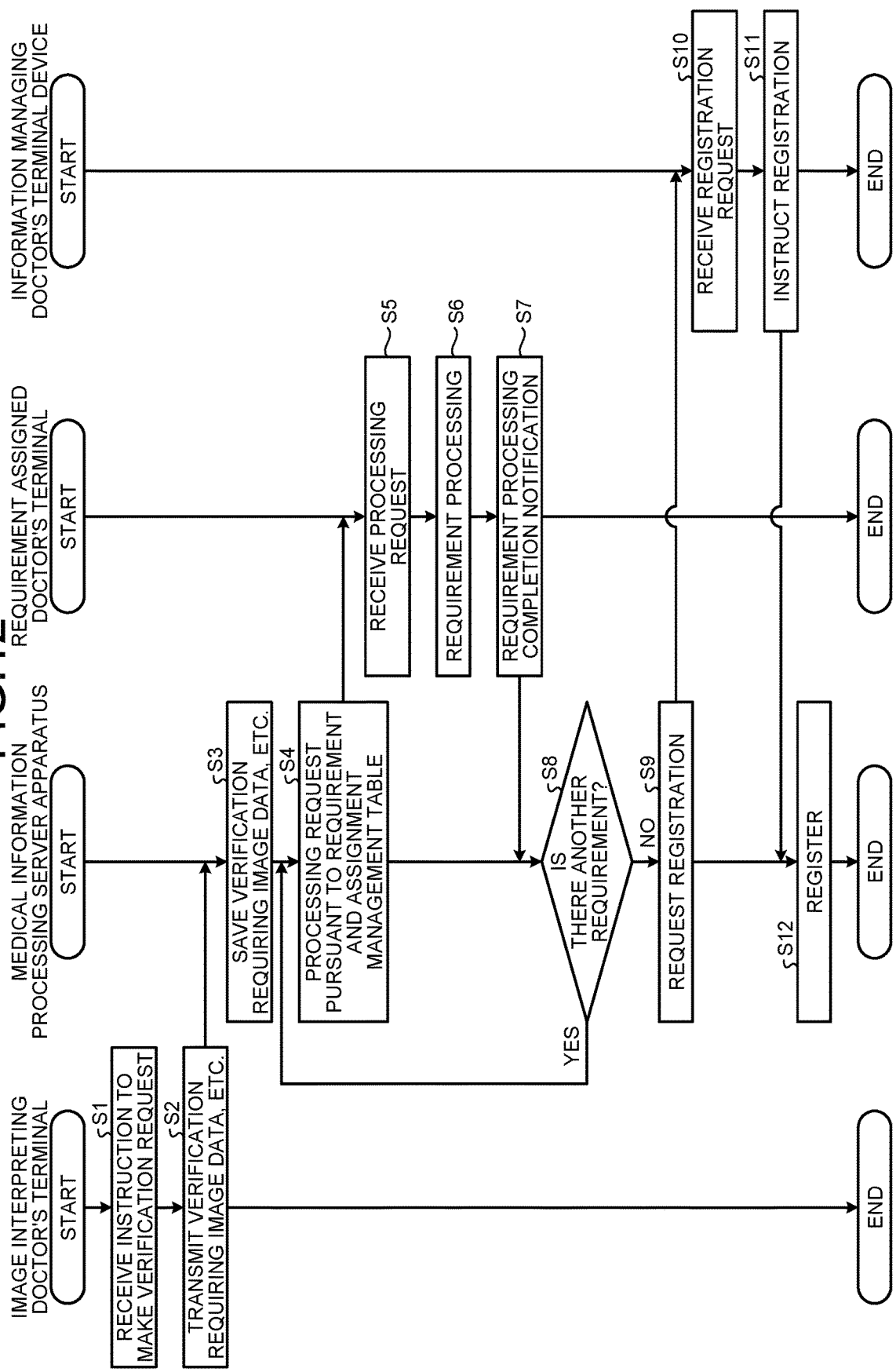

MEDICAL INFORMATION PROCESSING SYSTEM AND MEDICAL INFORMATION PROCESSING APPARATUS

CROSS-REFERENCE TO RELATED APPLICATIONS

This application is based upon and claims the benefit of priority from Japanese Patent Application No. 2020-056658, filed on Mar. 26, 2020; the entire contents of which are incorporated herein by reference.

FIELD

Embodiments described herein relate generally to a medical information processing system and a medical information processing apparatus.

BACKGROUND

In recent years, many Artificial Intelligence (AI) technical features have started being introduced to the medical field. For example, for computer-aided diagnosis processes using deep learning, a trained model among others is developed so as to receive an input of an image obtained by a medical image diagnosis apparatus such as an X-ray computed tomography apparatus and to output an image in which the contour of a region estimated as a disease is extracted, together with the name of the disease.

To develop such a trained model, it is necessary to prepare a large volume of medical information having high levels of precision, for the purpose of using the information as training data. Further, medical information having high levels of precision and having medically been verified is necessary not only for developing trained models for medical purposes, but also for academic and educational purposes and the like. However, in conventional medical information management, there is no system capable of easily acquiring a large volume of medical information having high levels of precision.

BRIEF DESCRIPTION OF THE DRAWINGS

FIG. 1 is a block diagram illustrating an exemplary configuration of a medical information processing system according to an embodiment;

FIG. 2 is a block diagram illustrating an exemplary configuration of an image interpreting doctor's terminal;

FIG. 5 is a block diagram illustrating an exemplary configuration of an information managing doctor's terminal;

FIG. 6 is a drawing illustrating an example of a requirement and assignment management table displayed as a Graphical User Interface (GUI) on a second display circuit by a second controlling function;

FIG. 12 is a flowchart illustrating an example of a flow in a verification completed image generating process.

DETAILED DESCRIPTION

Figure 3:
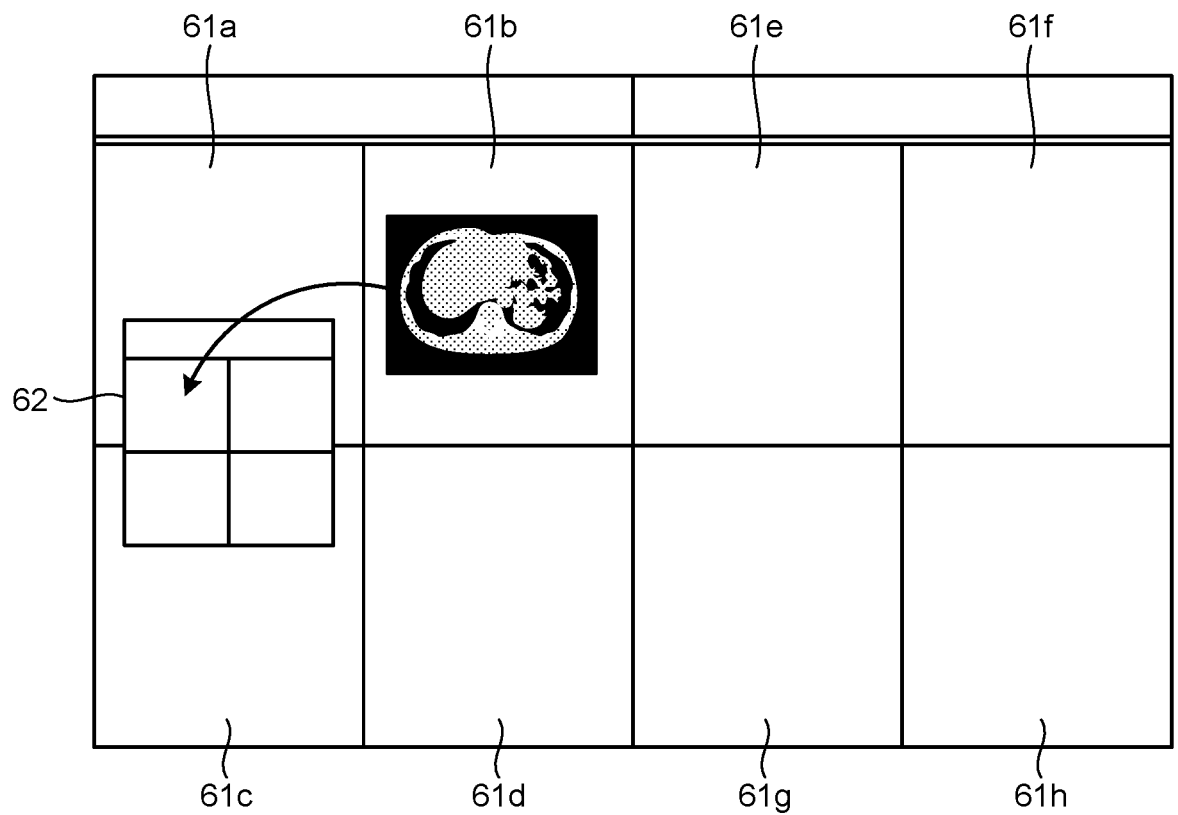
FIG. 3 is a drawing for explaining an example of an operation to instruct a verification request performed on the image interpreting doctor's terminal.

A medical information processing system according to an embodiment of the present disclosure includes a first processing circuit configured: to cause a display circuit to display a first image obtained by a medical image diagnosis apparatus; to cause the display circuit to display a plurality of regions classified in correspondence with a plurality of diseases and to display, in each of the plurality of regions, a representative image related to a corresponding one of the diseases; to receive a correspondence operation to bring the first image displayed by the display circuit into correspondence with one of the plurality of regions; and to cause, in response to the correspondence operation, a storage circuit to store therein, with respect to each of the diseases, the first image displayed by the display circuit as a verification requiring image related to the disease corresponding to the region brought into correspondence therewith.

Exemplary embodiments of a medical information processing system and a medical information processing apparatus will be explained below, with reference to the accompanying drawings.

To begin with, an overall configuration of a medical information processing system according to an embodiment of the present disclosure will be explained. FIG. 1 is a diagram illustrating: a medical information processing system S including an image interpreting doctor's terminal 1, an information managing doctor's terminal 2, a requirement assigned doctor's terminal 3, and a medical information processing server apparatus 4 serving as a medical information processing apparatus; an electronic medical record server apparatus 5; a radiology department information server apparatus 6; a medical image diagnosis apparatus 7, and a medical image management server apparatus 8. Alternatively, the medical information processing system S may include, as necessary, the electronic medical record server apparatus 5; the radiology department information server apparatus 6, the medical image diagnosis apparatus 7, and the medical image management server apparatus 8.

The apparatuses included in the medical information processing system S are capable of communicating with one another via a network N. Further, the apparatuses included in the medical information processing system S, the electronic medical record server apparatus 5, the radiology department information server apparatus 6, the medical image diagnosis apparatus 7, and the medical image management server apparatus 8 are capable of communicating with one another via the network N.

Typically, the medical information processing system S, the electronic medical record server apparatus 5, the radiology department information server apparatus 6, the medical image diagnosis apparatus 7, and the medical image management server apparatus 8 are installed in a hospital. In contrast, for example, the medical information processing server apparatus 4, the electronic medical record server apparatus 5, the radiology department information server apparatus 6, and the medical image management server apparatus 8 do not necessarily have to be installed in a hospital and may be installed anywhere, as long as the environment allows the apparatuses to communicate with one another via the network N. Further, the image interpreting doctor's terminal 1, the information managing doctor's terminal 2, and the requirement assigned doctor's terminal 3 may each be a mobile terminal (e.g., a notebook computer or a tablet computer) that is usable outside the hospital.

The electronic medical record server apparatus 5 and a terminal device (hereinafter, "electronic medical record terminal device") electrically connected to the electronic medical record server apparatus 5 structure an electronic medical record system. The electronic medical record system is an information system configured to manage electronic medical records for recording specifics of diagnosis/treatment processes. The electronic medical record server apparatus 5 is a computer device configured to execute processes related to managing the electronic medical records. The electronic medical record terminal device is used by medical doctors, nurses, and the like who input information to and reference the electronic medical records. The electronic medical record server apparatus 5 and the electronic medical record terminal device are connected to a communication network. According to an instruction from a clinician, the electronic medical record terminal device is configured to receive an input of a medical examination order (hereinafter, "examination order") for an examined subject (hereinafter, "patient"). When the examination order indicates imaging the patient in relation to an image diagnosis process, the examination order includes, for example, an examined site, an examination type (information related to specifics of the examination such as a modality), the name of a disease (hereinafter, "disease name"), an examination purpose, and the like. Further, the examination order may include other information such as a patient ID and the name of the patient undergoing the examination, an examination ID, the examination date, and the like. In response to the input of the examination order, the electronic medical record server apparatus 5 is configured to transmit the examination order to the radiology department information server apparatus 6, together with patient information of the patient, and the like.

The radiology department information server apparatus 6 and a terminal device (hereinafter, "radiology department terminal device") electrically connected to the radiology department information server apparatus 6 structure a radiology department information system (hereinafter, "Radiology Information System (RIS)"). The RIS is an information system configured to manage information in the radiology department of the hospital. The radiology department information server apparatus (hereinafter, "RIS server") 6 is a computer device configured to execute processes related to managing the information in the radiology department. As an example of an operation, the RIS server 6 is configured to receive the examination order from the electronic medical record server apparatus 5 and to obtain, from within the examination order, information (e.g., the examination type) related to the medical image diagnosis apparatus 7 and the like. The RIS server 6 is configured to transmit the examination order to the medical image diagnosis apparatus 7 specified in the examination order. When the examination order is transmitted to the medical image diagnosis apparatus 7, the RIS server 6 may append information such as the patient ID and the examination date to a Digital Imaging and Communications in Medicine (DICOM) tag or the like. The radiology department terminal device may be used by a radiology department doctor for creating an image interpretation report related to a medical image.

For example, the medical image diagnosis apparatus 7 is an apparatus configured to obtain medical images, such as an X-ray diagnosis apparatus, an X-ray Computed Tomography (CT) apparatus, or a Magnetic Resonance Imaging (MRI) apparatus. On the basis of the examination order from the RIS server 6 and in response to an operation to start an imaging process performed by a medical technologist or the like, the medical image diagnosis apparatus 7 is configured to perform the imaging process on the patient. As a result of executing the imaging process, the medical image diagnosis apparatus 7 is configured to acquire data indicating the state of a tissue inside the body of the patient. On the basis of the data, the medical image diagnosis apparatus 7 is configured to generate a medical image and to transmit the generated medical image to the medical image management server apparatus 8 together with the examination order. Further, the medical image diagnosis apparatus 7 is configured to transmit the generated medical image to the medical image management server apparatus 8.

The medical image management server apparatus 8 and a terminal device (hereinafter, "image management terminal device") electrically connected to the medical image management server apparatus 8 structure a medical image management system (hereinafter, "Picture Archiving and Communication System (PACS)"). The PACS is an information system configured to manage medical images such as X-ray CT images and MR images, as well as image interpretation reports, which may be called image diagnosis reports. The medical image management server apparatus (which hereinafter may be referred to as "PACS server") 8 is a computer device configured to execute processes related to managing the medical images. Upon receipt of the medical image and the examination order from the medical image diagnosis apparatus 7, the PACS server 8 is configured to store therein the medical image and the examination order so as to be kept in association with each other. The medical image has meta information (hereinafter, "additional information") of DICOM added thereto. The additional information includes the patient's name, a patient ID, explanation (e.g., the slice thickness, the slice number, and whether the image contrast was enhanced or not) about the medical image, and the like. The image management terminal device is, for example, used by a radiology department doctor for creating an image interpretation report.

The medical information processing system S is configured to perform a verification process using a verification requiring image and to perform a verification completed image generating process. In this situation, the "verification requiring image" denotes a medical image related to a specific disease selected by an image interpreting doctor on the image interpreting doctor's terminal 1. Further, the "verification process using the verification requiring image" denotes a process of verifying whether or not the disease diagnosed on the basis of the verification requiring image (i.e., an observation made on the basis of the verification requiring image) is appropriate. Further, the "verification completed image" denotes an image obtained when, for a verification requiring image, a sufficient level of precision to serve as a basis of the diagnosed disease has been guaranteed in the verification process. In this situation, the verification completed image may include, as additional information, verification information obtained as a result of the verification process. As information having a medically high level of precision, the verification completed image obtained by the medical information processing system S may be used as, for example, training-purpose data (learning-purpose data) in deep learning, academic-purpose data, or educational-purpose data.

The acquisition of the verification requiring image may be realized by, for example, the image interpreting doctor's terminal 1 and the medical information processing server apparatus 4. The verification process on verification requiring images and the obtaining and managing process of the verification information are realized by the information managing doctor's terminal 2, the requirement assigned doctor's terminal 3, and the medical information processing server apparatus 4. In the following sections, the image interpreting doctor's terminal 1, the information managing doctor's terminal 2, the requirement assigned doctor's terminal 3, and the medical information processing server apparatus 4 structuring the medical information processing system S will each be explained in detail.

The Image Interpreting Doctor's Terminal 1

The image interpreting doctor's terminal 1 is a computer such as a workstation used for reading and observing any of the images stored in the medical image management server apparatus 8. The image interpreting doctor observes images of each patient by using the image interpreting doctor's terminal 1 and writes observations in electronic medical records. Further, the image interpreting doctor's terminal 1 is configured to instruct the medical information processing server apparatus 4 to make a verification request regarding the verification requiring image. In the example in FIG. 1, the medical information processing system S includes the one image interpreting doctor's terminal 1. Alternatively, the medical information processing system S may include two or more image interpreting doctor's terminals 1.

FIG. 2 is a block diagram illustrating a configuration of the image interpreting doctor's terminal 1. As illustrated in FIG. 2, the image interpreting doctor's terminal 1 includes a first storage circuit 10, a first processing circuit 11, a first input circuit 12, a first communication I/F circuit 13, and a first display circuit 14.

The first storage circuit 10 is configured by using a semiconductor memory element such as a Random Access Memory (RAM) or a flash memory, or a hard disk, an optical disk, or the like. The first storage circuit 10 may be configured by using a portable media such as a Universal Serial Bus (USB) memory or a Digital Video Disk (DVD).

The first storage circuit 10 has stored therein various types of programs (which include application programs as well as an Operating System (OS) and the like) used by the first processing circuit 11, data necessary for executing the programs, volume data, and medical images. Further, the OS may include a Graphical User Interface (GUI) that uses many graphic elements for displaying information for the operator on the first display circuit 14 and on which it possible to perform basic operations through the first input circuit 12.

The first processing circuit 11 is a processor configured to realize functions corresponding to programs by reading and executing the programs from the first storage circuit 10. The first processing circuit 11 includes a first controlling function 110, for example. The first processing circuit 11 is configured to realize the first controlling function 110 by reading various types of control programs stored in the first storage circuit 10 and is also configured to integrally control processing operations of the first storage circuit 10, the first input circuit 12, the first communication I/F circuit 13, and the first display circuit 14. In other words, the first processing circuit 11 that has read the programs has the functions illustrated within the first processing circuit 11 in FIG. 2.

The first controlling function 110 is configured to cause the first display circuit 14 to display images (a first image) obtained by the medical image diagnosis apparatus 7, is also configured to cause the first display circuit 14 to display a plurality of regions classified in correspondence with a plurality of diseases and to display, in each of the plurality of regions, a representative image related to a corresponding one of the diseases, and is further configured to receive a correspondence operation that brings the first image displayed by the first display circuit 14 into correspondence with one of the plurality of regions. In this situation, the first controlling function 110 is an example of an operation controlling unit and an information processing controlling unit.

More specifically, at first, the first controlling function 110 reads the image obtained by the medical image diagnosis apparatus 7 and stored in the medical image management server apparatus 8 and causes the first display circuit 14 to display the read image. By observing the displayed image, the image interpreting doctor writes observations (e.g., what kind of disease, in which position in the image the disease is present) for the patient corresponding to the image, in the image and in an electronic medical record.

The first controlling function 110 causes the first display circuit 14 to display at least one region corresponding to at least one disease (e.g., which may be a plurality of windows corresponding to a plurality of diseases; hereinafter, "disease-specific window"). Further, in each of the plurality of regions classified in correspondence with the plurality of diseases included in the disease-specific window, the first controlling function 110 causes the first display circuit 14 to display the representative image related to the corresponding one of the diseases.

Further, in response to the correspondence operation that brings any of the images displayed by the first display circuit 14 into correspondence with one of the plurality of regions included in the disease-specific window, the first controlling function 110 transmits, to the medical information processing server apparatus 4, the image displayed by the first display circuit 14 as a verification requiring image related to the corresponding one of the diseases.

With reference to FIG. 2, the example was explained in which the single processor (the first processing circuit 11) realizes the first controlling function 110. However, another arrangement is also acceptable in which a processing circuit is structured by combining together a plurality of independent processors, so that the functions are realized as a result of the processors executing the programs. Further, with reference to FIG. 2, the example was explained in which the single storage circuit (the first storage circuit 10) has stored therein the programs corresponding to the processing functions. However, another arrangement is also acceptable in which a plurality of first storage circuits 10 are provided in a distributed manner, so that the first processing circuit 11 reads a corresponding program from each of the individual first storage circuits 10.

The term "processor" used in the above explanations denotes, for example, a Central Processing Unit (CPU), a Graphical Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The one or more processors realize the functions by reading and executing the programs saved in the first storage circuit 10. Alternatively, instead of saving the programs in the first storage circuit 10, it is also acceptable to directly incorporate the programs into the circuits of the one or more processors. In that situation, the one or more processors realize the functions by reading and executing the programs incorporated in the circuits thereof.

The first input circuit 12 is a circuit configured to receive inputs of signals from an input device such as a pointing device (e.g., a mouse), a keyboard, or the like being operable by the operator. In the present example, it is assumed that the input device itself is also included in the first input circuit 12. When the operator operates the input device, the first input circuit 12 is configured to generate an input signal corresponding to the operation and to output the generated input signal to the first processing circuit 11. In an example, the image interpreting doctor's terminal 1 may include a touch panel in which the input device is integrally formed with the first display circuit 14.

The first input circuit 12 is realized by using a trackball, a switch button, a mouse, a keyboard, a touchpad on which an input operation can be performed by touching an operation surface thereof, a touchpad on which an input operation can be performed by touching an operation surface thereof, a touch screen in which a display screen and a touchpad are integrally formed, a contactless input circuit using an optical sensor, an audio input circuit, a touch panel display device in which, a display screen and a touchpad are integrally formed, and/or the like that are used for setting a Region Of Interest (ROI) or the like.

The first input circuit 12 does not necessarily have to include physical operation component parts such as a mouse, a keyboard, and/or the like. Examples of the first input circuit 12 include, for instance, an electrical signal processing circuit configured to receive electrical signals corresponding to input operations from an external input device provided separately from the apparatus and to output the electrical signals to a control circuit.

Further, the first input circuit 12 is configured to receive the correspondence operation that brings any of the images displayed by the first display circuit 14 into correspondence with one of the plurality of regions included in the disease-specific window. The correspondence operation is realized by, for example, a drag-and-drop operation, an operation performed on a button, or the like. The correspondence operation corresponds to a selecting operation to select any of the images displayed by the first display circuit 14 that received a drag-and-drop operation as a verification requiring image and to the operation to instruct the medical information processing server apparatus 4 to make a verification request regarding the verification requiring image.

Next, the operation to request the verification request realized by the first controlling function 110 and the first input circuit 12 will be explained in detail, with reference to FIGS. 3 and 4.

Figure 4:
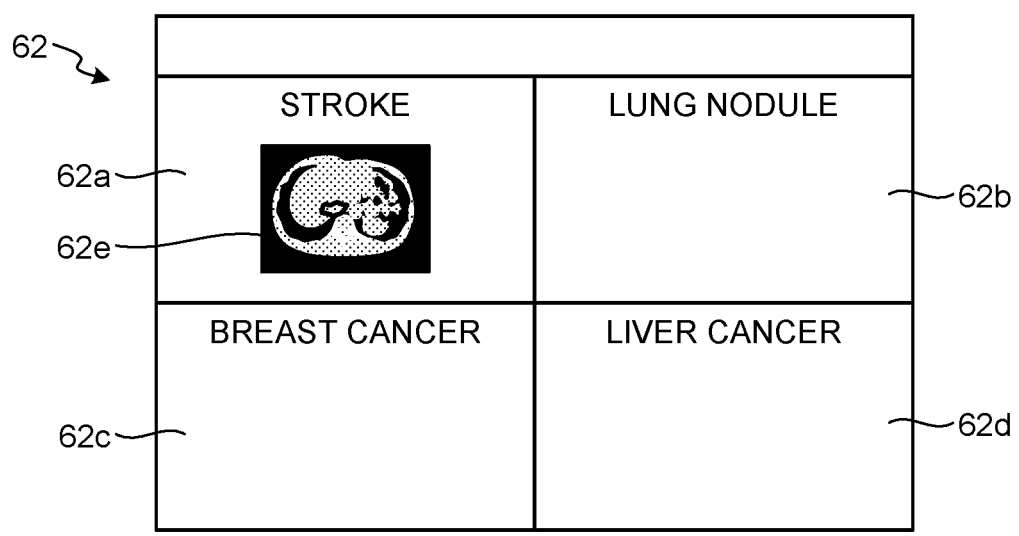
FIG. 4 is another drawing for explaining the example of the operation to instruct the verification request performed on the image interpreting doctor's terminal.

FIGS. 3 and 4 are drawings for explaining the operation to instruct the verification request performed on the image interpreting doctor's terminal 1 and illustrate examples of a plurality of images 61a to 61h to be interpreted by the image interpreting doctor and a disease-specific window 62. In the following sections, let us discuss an example in which the image interpreting doctor uses the image 61b in FIG. 3 as a key image (an image serving as a basis of a diagnosis) and determines a disease of the patient as a stroke, so that the image interpreting doctor's terminal 1 instructs the medical information processing server apparatus 4 to make a verification request, while using the key image 61b as a verification requiring image.

As illustrated in FIG. 3, the first display circuit 14 of the image interpreting doctor's terminal 1 displays, with regard to the patient, the plurality of images 61a to 61h read from the medical image management server apparatus 8. In response to an operation through the first input circuit 12, any of the displayed images may arbitrarily be replaced with another image. From among the plurality of images 61a to 61h taken during an examination, the image interpreting doctor determines the key image 61b as a basis of diagnosing the disease of the patient as a "stroke", draws a contour of the disease in the key image 61b and writes, in an electronic medical record, "stroke" as an observation as well as information about the position and the size thereof, and the like.

Further, as illustrated in FIGS. 3 and 4, the first display circuit 14 of the image interpreting doctor's terminal 1 displays the disease-specific window 62 together with the plurality of images 61a to 61h. FIGS. 3 and 4 illustrates an example in which the disease-specific window is classified into four regions (sub-windows) 62a to 62d corresponding to four diseases, namely, "stroke", "lung nodule", "breast cancer", and "liver cancer". The drawings merely illustrate an example. The number of sub-windows corresponding to the diseases and being classified in the disease-specific window is not limited. Further, it is also acceptable to display the plurality of windows so as to be superimposed on one another, so that a desired one of the windows is selected from displayed tabs or the like, for example.

Further, in each of the sub-windows 62a to 62d corresponding to the four diseases in the disease-specific window, a representative image related to the corresponding one of the diseases is displayed. FIG. 4 illustrates an example in which the sub-window 62a corresponding to "stroke" displays a representative image 62e.

While using the representative image 62e displayed in the sub-window 62a as a sample, the image interpreting doctor selects one of the plurality of images 61a to 61h displayed by the first display circuit 14 as a verification requiring image (i.e., the key image 61b in the present example). By using the selected verification requiring image and performing a drag-and-drop operation via the first input circuit 12, the image interpreting doctor performs a correspondence operation to bring the sub-window 62a corresponding to "stroke" into correspondence therewith. In response to the correspondence operation, the first controlling function 110 transmits, to the medical information processing server apparatus 4 via the first communication I/F circuit 13, image data of the key image 61b including additional information indicating the "stroke" as an observation, while using the key image 61b as the verification requiring image of the "stroke".

As a result, the image interpreting doctor's terminal 1 realizes instructing the medical information processing server apparatus 4 to make the verification request regarding the verification requiring image (i.e., transmitting the verification requiring image data including the additional information indicating the "stroke" as an observation). As explained later, in response to the verification request, the medical information processing server apparatus 4 acquires verification requiring images classified in correspondence with diseases.

Returning to the description of FIG. 2, the first communication I/F circuit 13 is configured to perform operations to communicate with external devices according to a prescribed communication standard. When the image interpreting doctor's terminal 1 is provided in a network, the first communication I/F circuit 13 is configured to transmit and receive information to and from external devices in the network. For example, the first communication I/F circuit 13 is configured to receive data obtained in imaging processes from the medical image diagnosis apparatus 7 and from the medical image management server apparatus 8.

The first display circuit 14 is a display device configured to display images and configured by using a Liquid Crystal Display (LCD) device or the like. In response to an instruction from the first processing circuit 11, the first display circuit 14 causes the LCD device to display various types of operation screens and various types of display information such as image data.

The Information Managing Doctor's Terminal 2

The information managing doctor's terminal 2 is a computer used by an information managing doctor. In the present example, the information managing doctor denotes a doctor who is authorized to approve and register, in a database, the verification completed image (including the additional information such as the verification information) that is eventually obtained as a result of executing the verification process on the verification requiring image.

FIG. 5 is a block diagram illustrating a configuration of the information managing doctor's terminal 2. As illustrated in FIG. 5, the information managing doctor's terminal 2 includes a second storage circuit 20, a second processing circuit 21, a second input circuit 22, a second communication I/F circuit 23, and a second display circuit 24. In this situation, because the second input circuit 22, the second communication I/F circuit 23, and the second display circuit 24 have substantially the same configurations as those of the first input circuit 12, the first communication I/F circuit 13, and the first display circuit 14, respectively, the explanations thereof will be omitted.

The second storage circuit 20 has the same hardware configuration as that of the first storage circuit 10. Further, the second storage circuit 20 has stored therein a dedicated program or the like for realizing the functions of the second processing circuit 21.

The second processing circuit 21 has the same hardware configuration as that of the first processing circuit 11. Further, the second processing circuit 21 is a processor configured to realize functions corresponding to programs by reading and executing the programs from the second storage circuit 20. The second processing circuit 21 includes a second controlling function 210, for example. The second processing circuit 21 is configured to realize the second controlling function 210 by reading various types of control programs stored in the second storage circuit 20 and is also configured to integrally control processing operations of the second storage circuit 20, the second input circuit 22, the second communication I/F circuit 23, and the second display circuit 24. In other words, the second processing circuit 21 that has read the programs has the functions illustrated within the second processing circuit 21 in FIG. 5.

The second controlling function 210 is configured to cause the second display circuit 24 to display, as a GUI, a "requirement and assignment management table" serving as a first management table that manages, with respect to each of the observations (diseases), one or more requirements and a person assigned to each of the one or more requirements. In the present example, the "requirement" denotes a condition required by the verification to be performed on a verification requiring image. Further, the "person assigned to each of the one or more requirements" denotes a medical doctor, a medical technologist, or the like, who will be in charge of processing regarding the requirement.

Further, the second controlling function 210 is configured to cause the second display circuit 24 to display, as a GUI, a progress management table serving as a second management table that classifies the requirements in correspondence with the assigned people and manages progress of each of the requirements.

FIG. 6 is a drawing illustrating an example of a requirement and assignment management table displayed as the GUI on the second display circuit 24 by the second controlling function 210. To explain a specific example, FIG. 6 illustrates the requirement and assignment management table used when an observation indicates a "stroke".

As illustrated in FIG. 6, in a verification process to endorse that the observation of a "stroke" is appropriate in response to an input from the second input circuit 22, the second controlling function 210 is able to set, as requirements, "contour extraction", "a result of a pathological examination", "genetic information", "approval on an image diagnosis result", and "final registration".

In this situation, "contour extraction" is a requirement related to an approval as to whether or not contour extraction of a region (the region corresponding to the stroke in the present example) serving as a basis of the observation regarding the verification requiring image is appropriate. The "result of a pathological examination" is a requirement requiring an approval as to whether the observation (the disease) is appropriate on the basis of a result of a pathological examination. The "genetic information" is a requirement requiring an approval as to whether the observation (the disease) is appropriate on the basis of a result of a genetic information. The "approval on an image diagnosis result" is a requirement requiring a final approval from a medical doctor who is responsible for the image diagnosis with regard to an observation created by using the verification requiring image. The "final registration" is a requirement requiring an approval for registering, in a database, a verification completed image obtained as a result of requirement processes that have been performed up to that point in time.

Further, as illustrated in FIG. 6, in response to an input from the second input circuit 22, the second controlling function 210 is able to set, as medical doctors or the like who will be assigned (hereinafter, "assigned doctors"), "Doctor a", "Doctor b", "Doctor c", and "Doctor d" to the requirements of the "contour extraction", the "result of a pathological examination", "the genetic information", the "approval on the image diagnosis result", and the "final registration". The assigned doctors or the like may be selected and changed by pressing a selection button 71, from among medical doctors and the like who are registered in advance.

Figures 7, 8:
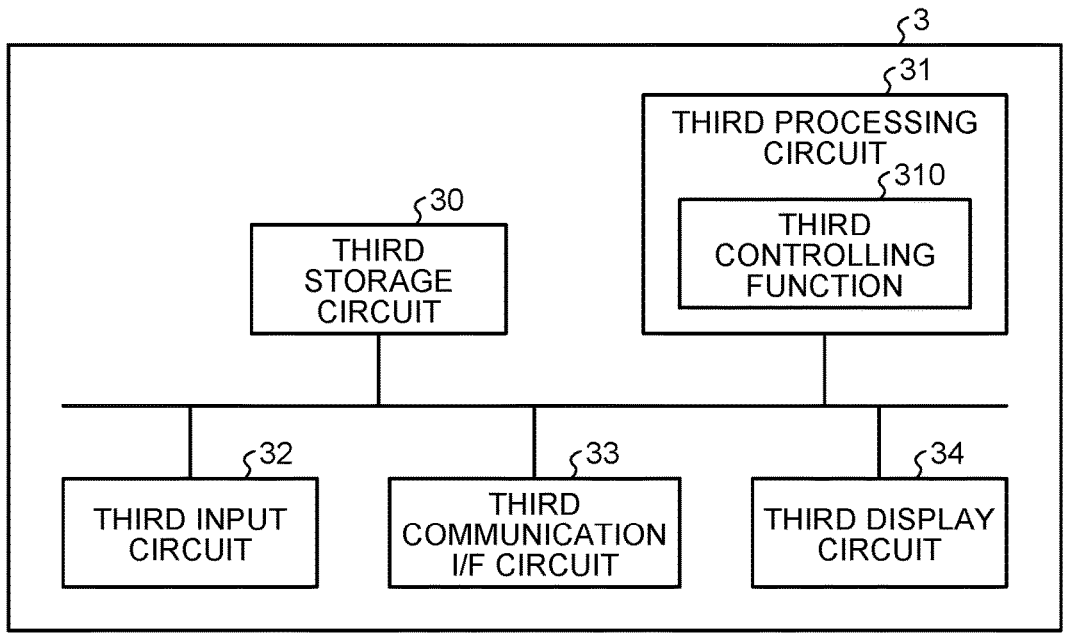
FIG. 7 is a drawing illustrating an example of a progress management table displayed as a GUI on the second display circuit by the second controlling function.
FIG. 8 is a block diagram illustrating an exemplary configuration of a requirement assigned doctor's terminal.

FIG. 7 is a drawing illustrating an example of the progress management table displayed as the GUI on the second display circuit 24 by the second controlling function 210. To explain a specific example, FIG. 7 illustrates the progress management table pursuant to the content of the requirement and assignment management table illustrated in FIG. 6.

As illustrated in FIG. 7, the second controlling function 210 is configured to generate the progress management table according to the content of the requirement and assignment management table and to update the progress management table according to processing completion notifications received from the requirement assigned doctor's terminal 3. In the progress management table illustrated in FIG. 7, the "data" denotes a data ID of the verification requiring image. The expression "OK" indicates that the processing corresponding to the requirement was executed by the assigned person. The expression "N/A (Not Applicable)" indicates that no processing corresponding to the requirement is necessary (i.e., no requirement is set in the requirement and assignment management table). The symbol "-" indicates that the processing corresponding to the requirement has not been executed by the assigned person. Further, if any of the requirement assigned doctors transmits a result indicating that "the verification requiring image does not qualify" from the requirement assigned doctor's terminal 3 due to a problem with the image quality or the like, the message to this effect is displayed in a corresponding section.

By viewing the progress management table, the information managing doctor is able to easily and promptly understand what stage the processing corresponding to each of the requirements has reached with respect to each of the verification requiring images and which doctor has not yet executed the requirement.

Further, the progress management table illustrated in FIG. 7 has a registration button 72 displayed, so as to be used by the information managing doctor to register the verification completed image obtained as a result of the verification process into a database. The information managing doctor is able to register the verification completed image into the database, by operating the registration button 72. Conversely, any image for which the registration button 72 has not been operated will not be registered as a verification completed image.

The Requirement Assigned Doctor's Terminal 3

The requirement assigned doctor's terminal 3 is a computer used by any of the assigned doctors set with the requirements in the requirement and assignment management table. By using the requirement assigned doctor's terminal 3, each of the doctors (the requirement assigned doctors) assigned to the requirements performs the processing of the requirement assigned to himself/herself, in response to a requirement processing request sent from the medical information processing server apparatus 4.

FIG. 8 is a block diagram illustrating a configuration of the requirement assigned doctor's terminal 3. As illustrated in FIG. 8, the requirement assigned doctor's terminal 3 includes a third storage circuit 30, a third processing circuit 31, a third input circuit 32, a third communication I/F circuit 33, and a third display circuit 34. In this situation, because the third input circuit 32, the third communication I/F circuit 33, and the third display circuit 34 have substantially the same configurations as those of the first input circuit 12, the first communication I/F circuit 13, and the first display circuit 14, respectively, the explanations thereof will be omitted.

The third storage circuit 30 has the same hardware configuration as that of the first storage circuit 10. Further, the third storage circuit 30 has stored therein a dedicated program or the like for realizing the functions of the third processing circuit 31.

The third processing circuit 31 has the same hardware configuration as that of the first processing circuit 11. Further, the third processing circuit 31 is a processor configured to realize functions corresponding to programs by reading and executing the programs from the third storage circuit 30. The third processing circuit 31 includes a third controlling function 310, for example. The third processing circuit 31 is configured to realize the third controlling function 310 by reading various types of control programs stored in the third storage circuit 30 and is also configured to integrally control processing operations of the third storage circuit 30, the third input circuit 32, the third communication I/F circuit 33, and the third display circuit 34. In other words, the third processing circuit 31 that has read the programs has the functions illustrated within the third processing circuit 31 in FIG. 8.

The third controlling function 310 is configured to receive the requirement processing request sent from the medical information processing server apparatus 4 and to prompt the requirement assigned doctor to perform the requirement processing. Further, the third controlling function 310 is configured to receive, from the medical information processing server apparatus 4, a "requirement processing management table" for managing the requirement processing assigned to the requirement assigned doctor and to cause the third display circuit 34 to display the received table. Further, the third controlling function 310 is configured to run an application program corresponding to the requirement processing assigned to the assigned doctor and to perform the requirement processing on the verification requiring image stored in the medical information processing server apparatus 4. Further, in response to a requirement processing completion operation performed through the third input circuit 32, the third controlling function 310 is configured to transmit a requirement processing completion notification to the medical information processing server apparatus 4.

Figures 9, 10:
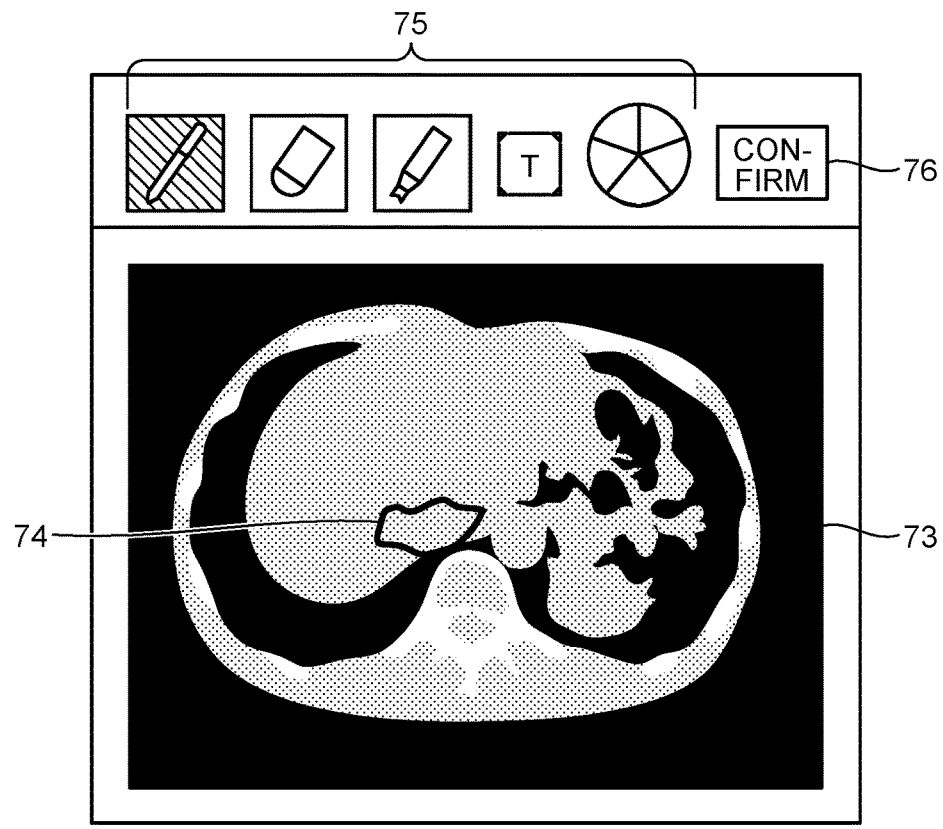
FIG. 9 is a drawing illustrating an example of a requirement processing management table displayed as a GUI on a third display circuit by a third controlling function.
FIG. 10 is a drawing illustrating an example of a screen displayed by an application program used for extracting a contour of a stroke.

FIG. 9 is a drawing illustrating an example of the requirement processing management table displayed as a GUI on the third display circuit 34 by the third controlling function 310. To explain a specific example, FIG. 9 illustrates the requirement processing management table used by the requirement assigned doctor's terminal 3 of the doctor assigned to the requirement of "contour extraction of a stroke".

The requirement processing management table may be displayed by the second display circuit 24 with timing desired by the requirement assigned doctor. The requirement processing management table displays, in a list form, images A, B, and C or the like on which the requirement assigned doctor has been requested to perform a stroke contour extracting process. Further, with respect to each of the images, a patient ID, the examination date, and the requesting doctor who requested the requirement processing are displayed.

By using the requirement processing management table, the requirement assigned doctor is able to manage the stroke contour extraction, with respect to each of the images for which the requirement processing request was received. Further, for example, by clicking on a desired one (e.g., image A) of the images in the requirement processing management table, the requirement assigned doctor is able to open an application program used for extracting the contour of the stroke.

FIG. 10 is a drawing illustrating an example of a GUI screen displayed by the application program used for extracting the contour of the stroke. The screen illustrated in FIG. 10 displays a verification requiring image 73, a contour line 74 of the stroke extracted from the verification requiring image 73, a contour line generating tool 75, and a confirmation button 76.

The requirement assigned doctor observes the contour line 74 serving as an observation from the verification requiring image 73 displayed on the screen and judges whether or not the contour line 74 is appropriate. When the contour line 74 is not appropriate, the requirement assigned doctor corrects the contour line 74 by using the contour line generating tool 75. After determining the contour line 74 presented as the observation is appropriate or after correcting the contour line 74 presented as the observation, the requirement assigned doctor completes the requirement processing on the image, by pressing the confirmation button 76 provided in the upper right section.

In response to the operation performed on the confirmation button 76, the third controlling function 310 is configured to transmit the requirement processing completion notification to the medical information processing server apparatus 4. In another example, in addition to the confirmation button 76, another button may be provided so as to collectively transmit a completion notification to the medical information processing server apparatus 4, when all the requirement processing processes of the requirement assigned doctor have been completed.

Further, if necessary, when any of the requirement assigned doctors determines that the "verification requiring image does not qualify" with respect to one or more of the images for which the requirement processing request was received, the requirement assigned doctor may transmit the judgment result from the requirement assigned doctor's terminal 3 to the medical information processing server apparatus 4.

The Medical Information Processing Server Apparatus 4

The medical information processing server apparatus 4 is configured to receive the request to verify the verification requiring image from the image interpreting doctor's terminal 1, is also configured to generate and update the requirement and assignment management table, the progress management table, and the requirement processing management table while communicating with the information managing doctor's terminal 2 and the requirement assigned doctor's terminal 3, and is further configured to generate medical information including the verification completed images.

Figure 11:
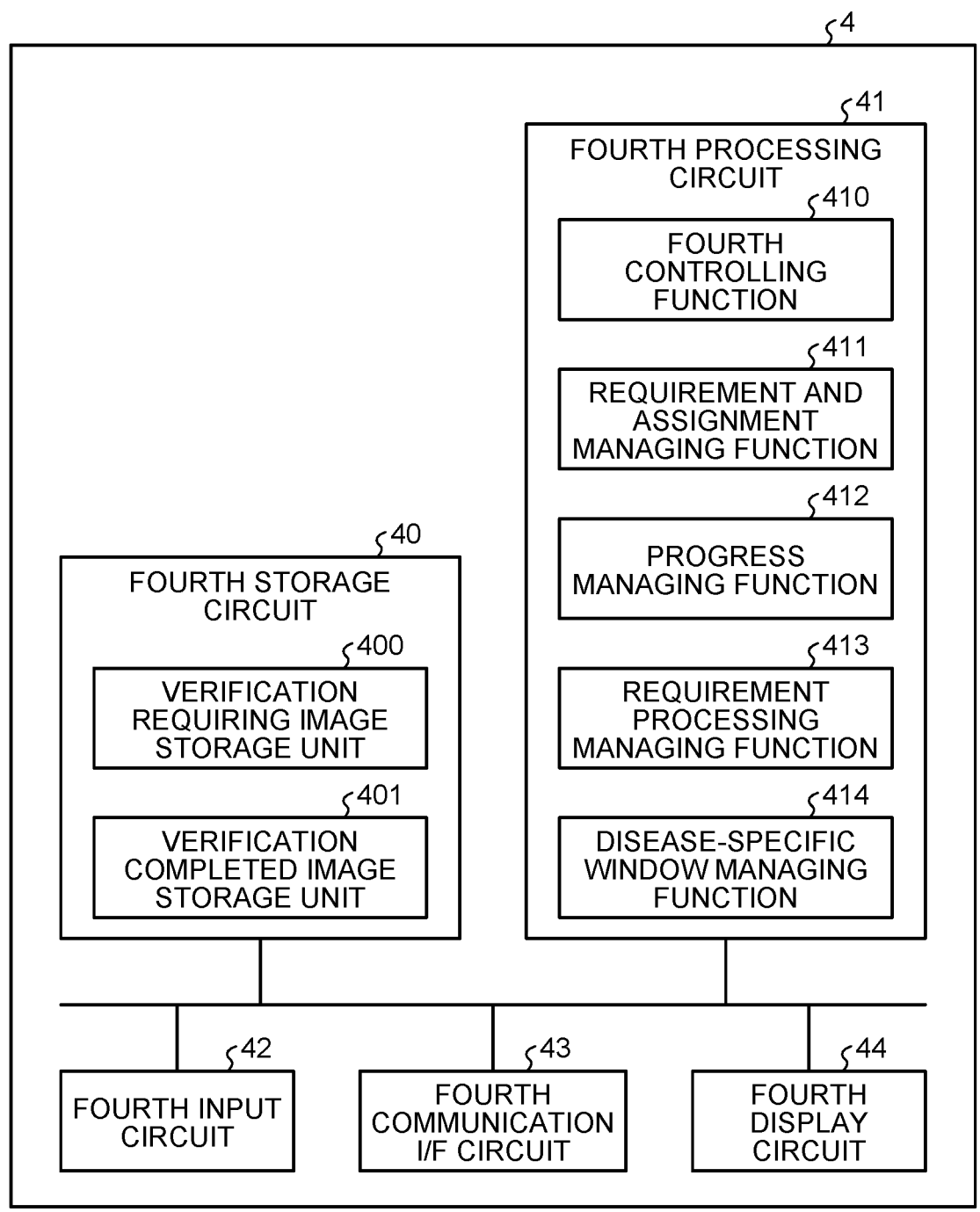
FIG. 11 is a block diagram illustrating an exemplary configuration of a medical information processing server apparatus.

FIG. 11 is a block diagram illustrating a configuration of the medical information processing server apparatus 4. As illustrated in FIG. 11, the medical information processing server apparatus 4 includes a fourth storage circuit 40, a fourth processing circuit 41, a fourth input circuit 42, a fourth communication I/F circuit 43, and a fourth display circuit 44. In this situation, because the fourth input circuit 42, the fourth communication I/F circuit 43, and the fourth display circuit 44 have substantially the same configurations as those of the first input circuit 12, the first communication I/F circuit 13, and the first display circuit 14, respectively, the explanations thereof will be omitted.

The fourth storage circuit 40 has the same hardware configuration as that of the first storage circuit 10. Further, the fourth storage circuit 40 has stored therein a dedicated program or the like for realizing the functions of the fourth processing circuit 41.

Further, the fourth storage circuit 40 includes a verification requiring image storage unit 400 and a verification completed image storage unit 401. The verification requiring image storage unit 400 is a database storing therein and managing the verification requiring images for which the verification requests were received from the image interpreting doctor's terminal 1 and the verification requiring images which have undergone the requirement processing by the requirement assigned doctor's terminal 3. The verification completed image storage unit 401 is a database storing therein and managing the verification completed images on which the requirement processing has been performed and which have undergone a registering process performed by the information managing doctor.

The fourth processing circuit 41 has the same hardware configuration as that of the first processing circuit 11. Further, the fourth processing circuit 41 is a processor configured to realize functions corresponding to programs by reading and executing the programs from the fourth storage circuit 40. The fourth processing circuit 41 includes, for example, a fourth controlling function 410, a requirement and assignment managing function 411, a progress managing function 412, a requirement processing managing function 413, and a disease-specific window managing function 414. The fourth processing circuit 41 is configured to realize the fourth controlling function 410, the requirement and assignment managing function 411, the progress managing function 412, the requirement processing managing function 413, and the disease-specific window managing function 414 by reading various types of control programs stored in the fourth storage circuit 40 and is also configured to integrally control processing operations of the fourth storage circuit 40, the fourth input circuit 42, the fourth communication I/F circuit 43, and the fourth display circuit 44. In other words, the fourth processing circuit 41 that has read the programs has the functions illustrated within the fourth processing circuit 41 in FIG. 11.

In response to the correspondence operation received from the image interpreting doctor's terminal 1, the fourth controlling function 410 is configured to cause the verification requiring image storage unit 400 of the fourth storage circuit 40 to store therein, with respect to each of the diseases, the verification requiring image serving as the first image and being displayed by the first display circuit 14 of the image interpreting doctor's terminal 1, as an image related to the disease corresponding to the region that was brought into correspondence therewith by the correspondence operation. Further, according to the requirement and assignment management table, the fourth controlling function 410 is configured to transmit a notification to request the requirement processing to the requirement assigned doctor's terminal 3. Also, in response to a registration instruction from the information managing doctor's terminal 2, the fourth controlling function 410 is configured to cause the verification completed image storage unit 401 of the fourth storage circuit 40 to store therein, with respect to each of the diseases, the verification requiring image on which the requirement processing processes have been performed, as a verification completed image. In this situation, the fourth controlling function 410 is an example of an information processing controlling unit.

The requirement and assignment managing function 411 is configured to generate the requirement and assignment management table (see FIG. 6). Further, the requirement and assignment managing function 411 is configured to change (update) the requirement and assignment management table according to a change operation received from the information managing doctor's terminal 2, for example.

The progress managing function 412 is configured to generate the progress management table (see FIG. 7). Further, the progress managing function 412 is configured to update the progress management table according to the requirement processing completion notification from the requirement assigned doctor's terminal 3.

The requirement processing managing function 413 is configured to generate the requirement processing management table (see FIG. 9). Further, the progress managing function 412 is configured to update the requirement processing managing table, according to the verification request from the image interpreting doctor's terminal 1 and the requirement processing completion notification from the requirement assigned doctor's terminal 3.

The disease-specific window managing function 414 is configured to manage the representative image with respect to each of the diseases in the disease-specific window displayed on the image interpreting doctor's terminal 1. In other words, the disease-specific window managing function 414 is configured to transmit, to the image interpreting doctor's terminal 1, the data used for displaying the disease-specific window including the representative image corresponding to each of the diseases on the image interpreting doctor's terminal 1.

Next, a verification completed image generating process realized by the medical information processing system S will be explained. To explain a specific example in the following sections, a situation will be explained in which a verification completed image is generated as training-purpose data (learning-purpose data) for deep learning.

FIG. 12 is a flowchart illustrating a flow in the verification completed image generating process.

As illustrated in FIG. 12, at first, by using the image interpreting doctor's terminal 1, the image interpreting doctor performs a drag-and-drop operation in the disease-specific window, with respect to a key image of which the image quality or the like was determined to be appropriate as learning-purpose data. The first controlling function 110 of the image interpreting doctor's terminal 1 receives the instruction to make a verification request as a result of the drag-and-drop operation (step S1). Further, in response to the drag-and-drop operation, the first controlling function 110 transmits verification requiring image data including the additional information such as an observation, to the medical information processing server apparatus 4 (step S2).

The fourth controlling function 410 of the medical information processing server apparatus 4 receives the verification requiring image including the additional information such as the observation and saves the verification requiring image into the fourth storage circuit 40 so as to be classified in correspondence with the disease (step S2). It should be noted that the processes at steps S1 through S3 may be performed as many times as desired, with timing desired by the image interpreting doctor.

The fourth controlling function 410 of the medical information processing server apparatus 4 notifies the requirement assigned doctor's terminal 3 of a requirement processing request, according to the generated requirement and assignment management table (step S4).

The third controlling function 310 of the requirement assigned doctor's terminal 3 receives the requirement processing request (step S5) and performs the requirement processing according to an input made by the requirement assigned doctor through the third input circuit 32 (step S6). The processes at steps S5 and S6 are repeatedly performed as many times as the number of requirement processing processes to be performed by the requirement assigned doctor. Further, when all the requirement processing processes performed by the requirement assigned doctor have been completed or every time one of the requirement processing processes performed by the requirement assigned doctor has been completed, the third controlling function 310 of the requirement assigned doctor's terminal 3 transmits a requirement processing completion notification to the medical information processing server apparatus 4 (step S7).

In response to the requirement processing completion notification from the requirement assigned doctor's terminal 3, the fourth controlling function 410 of the medical information processing server apparatus 4 judges whether or not a next requirement is present according to the requirement and assignment management table (step S8). When the fourth controlling function 410 of the medical information processing server apparatus 4 determines that a next requirement is present (step S8: Yes), the processes at steps S4 through S7 are repeatedly performed. On the contrary, when the fourth controlling function 410 of the medical information processing server apparatus 4 determines that no next requirement is present (step S8: No), the fourth controlling function 410 of the medical information processing server apparatus 4 transmits a registration request to the information managing doctor's terminal 2 to have the verification requiring image registered as a verification completed image (step S9).

The second controlling function 210 of the information managing doctor's terminal 2 receives the registration request from the medical information processing server apparatus 4 (step S10), receives the registration instruction according to an input made by the information managing doctor through the second input circuit 22, and also transmits the registration instruction to the medical information processing server apparatus 4 (step S11).

In response to the registration instruction from the information managing doctor's terminal 2, the fourth controlling function 410 of the medical information processing server apparatus 4 causes the verification completed image storage unit 401 to store therein the verification requiring image on which the requirement processing processes have been performed, as a verification completed image (step S11).

As explained above, the medical information processing system S according to the present embodiment includes the first controlling function 110 serving as an operation controlling unit and the fourth controlling function 410 serving as a controlling unit. The first controlling function 110 is configured to cause the first display circuit 14 to display the first image obtained by the medical image diagnosis apparatus 7 and to cause the first display circuit 14 to display the disease-specific window 62 presented as the plurality of regions corresponding to the plurality of diseases and the representative images corresponding to the diseases in the disease-specific window 62. Further, the first controlling function 110 is configured to receive, via the first input circuit 12, the correspondence operation to bring the first image displayed by the first display circuit 14 into correspondence with one of the regions in the disease-specific window 62. In response to the correspondence operation, the fourth controlling function 410 is configured to cause the verification requiring image storage unit 400 to store therein, with respect to each of the diseases, the first image displayed by the first display circuit 14, as the verification requiring image related to the disease corresponding to the region brought into correspondence therewith.

The image interpreting doctor is able to accumulate any images selected thereby in the verification requiring image storage unit 400 of the medical information processing server apparatus 4 as the verification requiring images, by referring to the representative images displayed on the image interpretation work screen and performing simple operations on the screen. Consequently, without being burdened, the doctor is able to easily acquire a large volume of medical information having high levels of precision, while performing regular image interpretation work.

Further, the medical information processing system S according to the present embodiment includes the requirement and assignment managing function 411 serving as a first managing unit. The requirement and assignment managing function 411 is configured to generate the requirement and assignment management table that manages, with respect to each of the plurality of diseases, the one or more requirements necessary for the verification process and the person assigned to each of the one or more requirements. According to the requirement and assignment management table, the fourth controlling function 410 is configured to transmit, to each of the assigned people, the processing request so as to have the corresponding requirement processed.

Consequently, by using the requirement and assignment management table, it is possible to manage, with respect to each of the diseases, the requirements necessary for the verification process and the doctors assigned to the requirements. Further, by receiving the processing request regarding the requirements necessary for the verification process assigned to him/her, each of the requirement assigned doctors is able to recognize what processing needs be performed on the verification requiring images accumulated in the verification requiring image storage unit 400 of the medical information processing server apparatus 4.

Further, when there are two or more requirements, the requirement and assignment managing function 411 is configured to generate the requirement and assignment management table so as to include the sequential order in which the two or more requirements are to be performed. To each of the assigned people, the fourth controlling function 410 is configured to transmit the processing request according to the sequential order. Consequently, by receiving the processing request pursuant to the sequential order, each of the requirement assigned doctors is able to perform the requirement processing using what has been processed by the requirement assigned doctors on the previous stages.

Further, the medical information processing system S according to the present embodiment includes the progress managing function 412 serving as a second managing unit. The progress managing function 412 is configured to generate the progress management table that manages the progress of each of the requirements by classifying the assigned people and the requirements with respect to each of the verification requiring images and to update the progress management table on the basis of the completion notifications transmitted from the assigned people. Consequently, by using the progress management table, it is possible to manage, with respect to each of the diseases, the progress status of each of the requirements and the working status of each of the assigned doctors.

Further, in the medical information processing system S according to the present embodiment, the fourth controlling function 410 is configured, in response to the approval operation from the information managing doctor's terminal 2, to register the verification completed images obtained as a result of the verification processes performed on the verification requiring images, into the verification completed image storage unit 401. Consequently, it is possible to automatically and easily acquire the large volume of medical information having high levels of precision, after going through the processes of verification request from the image interpreting doctor, the verification processes performed by the requirement assigned doctors regarding the requirements, and the final approval from the information managing doctor.

First Modification Example

The above embodiments of the present disclosure use the example of the medical information processing system S including the image interpreting doctor's terminal 1, the information managing doctor's terminal 2, the requirement assigned doctor's terminal 3, and the medical information processing server apparatus 4 that are separate from one another. However, possible embodiments are not limited to this example. It is also acceptable to partially integrate two or more of the devices among the image interpreting doctor's terminal 1, the information managing doctor's terminal 2, the requirement assigned doctor's terminal 3, and the medical information processing server apparatus 4, for example, by integrating the information managing doctor's terminal 2 with the medical information processing server apparatus 4 as a single device.

Second Modification Example

In the requirement and assignment management table illustrated in FIG. 6, it is also acceptable to set two or more requirement assigned doctors or the like with respect to each of the requirements. In that situation, it is acceptable to determine priority levels among the plurality of requirement assigned doctors or the like being set, so as to issue the requirement processing requests according to the order of priority levels.

Further, in the requirement and assignment management table illustrated in FIG. 6, it is also acceptable to share, among a plurality of people, the role of the requirement assigned doctor or the like with respect to each of the requirements. In that situation, it is possible to make a request to an assigned person having a smaller workload, in accordance with the volume requested of each of the assigned people.

Further, when two or more people are set as the requirement assigned doctors or the like with respect to each of the requirements, it is also acceptable to calculate reliability in the requirement processing, with respect to each of the assigned people.

Further, in the requirement and assignment management table illustrated in FIG. 6, it is also acceptable to set a processing time limit with respect to each of the requirements, so as to automatically transmit a processing request again when the time limit is passed. Further, when there is more than one assigned person and the time limit being set is passed, a request may be made to another assigned person according to priority levels. The information managing doctor is thus able to manage the progress further in detail by checking the progress and using the processing time limits being set.

At least one aspect of the embodiments described above makes it possible to easily acquire the large volume of medical information having high levels of precision.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:
1. A medical information processing system, comprising:
a first processing circuit configured to:
cause a display circuit to display a first image obtained by a medical image diagnosis apparatus;
cause the display circuit to display a plurality of regions classified in correspondence with a plurality of diseases and to display, in each of the plurality of regions, a representative image that is related to a corresponding one of the diseases and is different from the first image;

receive a correspondence operation to bring the first image displayed by the display circuit into correspondence with a particular region of the plurality of regions displayed by the display circuit; and cause, in response to the correspondence operation, a storage circuit to store therein, with respect to each of the diseases, the first image displayed by the display circuit as a verification-requiring image related to the disease corresponding to the particular region displayed by the display circuit and brought into correspondence therewith.

2. The medical information processing system according to claim 1, further comprising a second processing circuit configured to:

generate a first management table that manages, with respect to each of the plurality of diseases, one or more requirements necessary for a verification process and a person assigned to each of the one or more requirements; and transmit a processing request for having the corresponding requirement processed, to each of the assigned persons according to the first management table.

3. The medical information processing system according to claim 2, wherein when there are two or more requirements, the second processing circuit is further configured to generate the first management table so as to include a sequential order in which the plurality of requirements are to be executed, and the second processing circuit is further configured to transmit the processing requests according to the sequential order of execution.

4. The medical information processing system according to claim 2, wherein the second processing circuit is further configured to:

classify the requirements in correspondence with the verification-requiring images, generate a second management table that manages progress of each of the requirements, and update the second management table based on a completion notification transmitted from each of the assigned persons.

5. The medical information processing system according to claim 2, wherein, in response to an approval operation, the second processing circuit is further configured to register a verification completed image obtained as a result of the verification process performed on the verification-requiring image.

6. The medical information processing system according to claim 2, wherein each of the one or more requirements includes one of the following: an approval by an information manager on registration; an approval by a person responsible for an image diagnosis: an approval on a contour line of a disease rendered in the verification requiring image: an approval based on pathological information; and an approval based on genetic information.

7. The medical information processing system of claim 1, wherein the first processing circuit is configured to cause the display circuit to display each of the representative images in the plurality of regions prior to receiving any correspondence operations.

8. A medical information processing apparatus, comprising:

a first processing circuit configured to:

cause a display circuit to display a first image obtained by a medical image diagnosis apparatus;

cause the display circuit to display a plurality of regions classified in correspondence with a plurality of diseases and to display, in each of the plurality of regions, a representative image that is related to a corresponding one of the diseases and is different from the first image;

receive a correspondence operation to bring the first image displayed by the display circuit into correspondence with a particular region of the plurality of regions displayed by the display circuit; and cause, in response to the correspondence operation, a storage circuit to store therein, with respect to each of the diseases, the first image displayed by the display circuit as a verification-requiring image related to the disease corresponding to the particular region displayed by the display circuit and brought into correspondence therewith.

9. The medical information processing apparatus according to claim 8, further comprising a second processing circuit configured to:

generate a first management table that manages, with respect to each of the plurality of diseases, one or more requirements necessary for a verification process and a person assigned to each of the one or more requirements; and transmit a processing request for having the corresponding requirement processed, to each of the assigned persons according to the first management table.

10. The medical information processing apparatus according to claim 9, wherein when there are two or more requirements, the second processing circuit is further configured to generate the first management table so as to include a sequential order in which the plurality of requirements are to be executed, and the second processing circuit is further configured to transmit the processing requests according to the sequential order of execution.

11. The medical information processing apparatus according to claim 9, wherein the second processing circuit is further configured to:

classify the requirements in correspondence with the verification-requiring images, generate a second management table that manages progress of each of the requirements, and update the second management table based on a basis of a completion notification transmitted from each of the assigned persons.

12. The medical information processing apparatus according to claim 9, wherein, in response to an approval operation, the second processing circuit is further configured to register a verification completed image obtained as a result of the verification process performed on the verification-requiring image.

13. The medical information processing apparatus according to claim 9, wherein each of the one or more requirements includes one of the following: an approval by an information manager on registration; an approval by a person responsible for an image diagnosis; an approval on a contour line of a disease rendered in the verification requiring image; an approval based on pathological information; and an approval based on genetic information.

14. A medical information processing method, comprising:

causing a display circuit to display a first image obtained by a medical image diagnosis apparatus;

causing the display circuit to display a plurality of regions classified in correspondence with a plurality of diseases and to display, in each of the plurality of regions, a representative image that is related to a corresponding a particular region of the diseases and is different from the first image;

receiving a correspondence operation to bring the first image displayed by the display circuit into correspondence with one of the plurality of regions displayed by the display circuit; and causing, in response to the correspondence operation, a storage circuit to store therein, with respect to each of the diseases, the first image displayed by the display circuit as a verification requiring image related to the disease corresponding to the particular region displayed by the display circuit and brought into correspondence therewith.

15. The medical information processing method according to claim 14, further comprising:

generating a first management table that manages, with respect to each of the plurality of diseases, one or more requirements necessary for a verification process and a person assigned to each of the one or more requirements; and transmitting a processing request for having the corresponding requirement processed, to each of the assigned persons according to the first management table.

16. The medical information processing method according to claim 15, wherein when there are two or more requirements, the method further includes generating the first management table so as to include a sequential order in which the plurality of requirements are to be executed, and the method further includes transmitting the processing requests according to the sequential order of execution.

17. The medical information processing method according to claim 15, further comprising:

classifying the requirements in correspondence with the verification-requiring images;

generating a second management table that manages progress of each of the requirements; and updating the second management table based on a completion notification transmitted from each of the assigned persons.

18. The medical information processing method according to claim 15, further comprising registering, in response to an approval operation, a verification completed image obtained as a result of the verification process performed on the verification requiring image.

19. The medical information processing method according to claim 15, wherein each of the one or more requirements includes one of the following: an approval by an information manager on registration; an approval by a person responsible for an image diagnosis; an approval on a contour line of a disease rendered in the verification requiring image; an approval based on pathological information; and an approval based on genetic information.

* * * * *